United States Patent [19]

Guerci

[11] Patent Number: 5,171,146

[45] Date of Patent: Dec. 15, 1992

[54] SYRINGE FOR WASHING TEETH ROOT CANALS

[76] Inventor: Sergio Guerci, Strada Collerolletta 27, 05100 Terni, Italy

[21] Appl. No.: 817,554

[22] Filed: Jan. 7, 1992

Related U.S. Application Data

[63] Continuation-in-part of Ser. No. 761,796, Sep. 16, 1991.

[30] Foreign Application Priority Data

Jan. 16, 1989 [IT]  Italy .............................. 52601/89[U]

[51] Int. Cl.$^5$ ............................................. A61G 5/02
[52] U.S. Cl. ...................................... 433/81; 433/80; 433/224
[58] Field of Search .................. 433/81, 80, 88, 89, 433/224

[56]  References Cited

U.S. PATENT DOCUMENTS

| | | | |
|---|---|---|---|
| 2,773,501 | 12/1956 | Young | 433/81 |
| 3,745,655 | 7/1973 | Malmin | 433/81 |
| 3,807,048 | 4/1974 | Malmin | 433/81 |
| 3,816,921 | 6/1974 | Malmin | 433/81 |
| 3,949,748 | 4/1976 | Malmin | 433/81 |

Primary Examiner—John J. Wilson
Attorney, Agent, or Firm—Millen, White, Zelano and Branigan

[57] ABSTRACT

A syringe useful for washing root canals wherein the syringe is configured and arranged with a two-position valve which, in a first position, supplies the syringe with hydrogen perioxide and, in the second position, supplies the syringe with sodium peroxide. In a selected embodiment, the valve has a single outlet port and first and second inlet ports connected to a hydrogen peroxide and sodium peroxide supply, respectively. The outlet port is connected to the inlet ports by a rotatable obturator having first and second slanted grooves having first and second ducts, respectively, at opposite ends thereof. In a first rotatable position of the obturator, the first groove is aligned with the first inlet port, and the first duct is aligned with the outlet port. In a second rotatable position of the obturator, the second groove is aligned with the second inlet port, and the second duct is aligned with the outlet port.

7 Claims, 5 Drawing Sheets

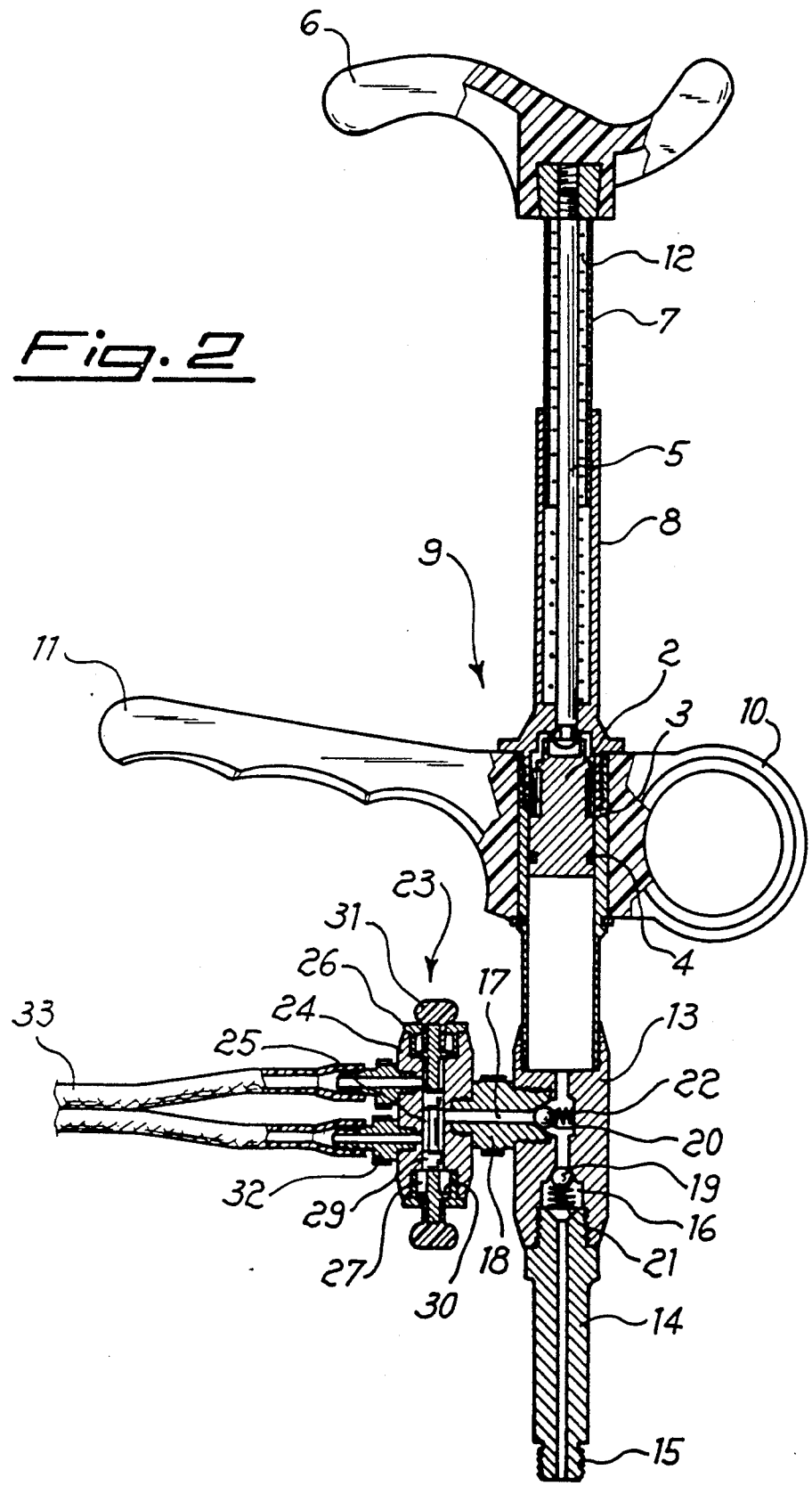

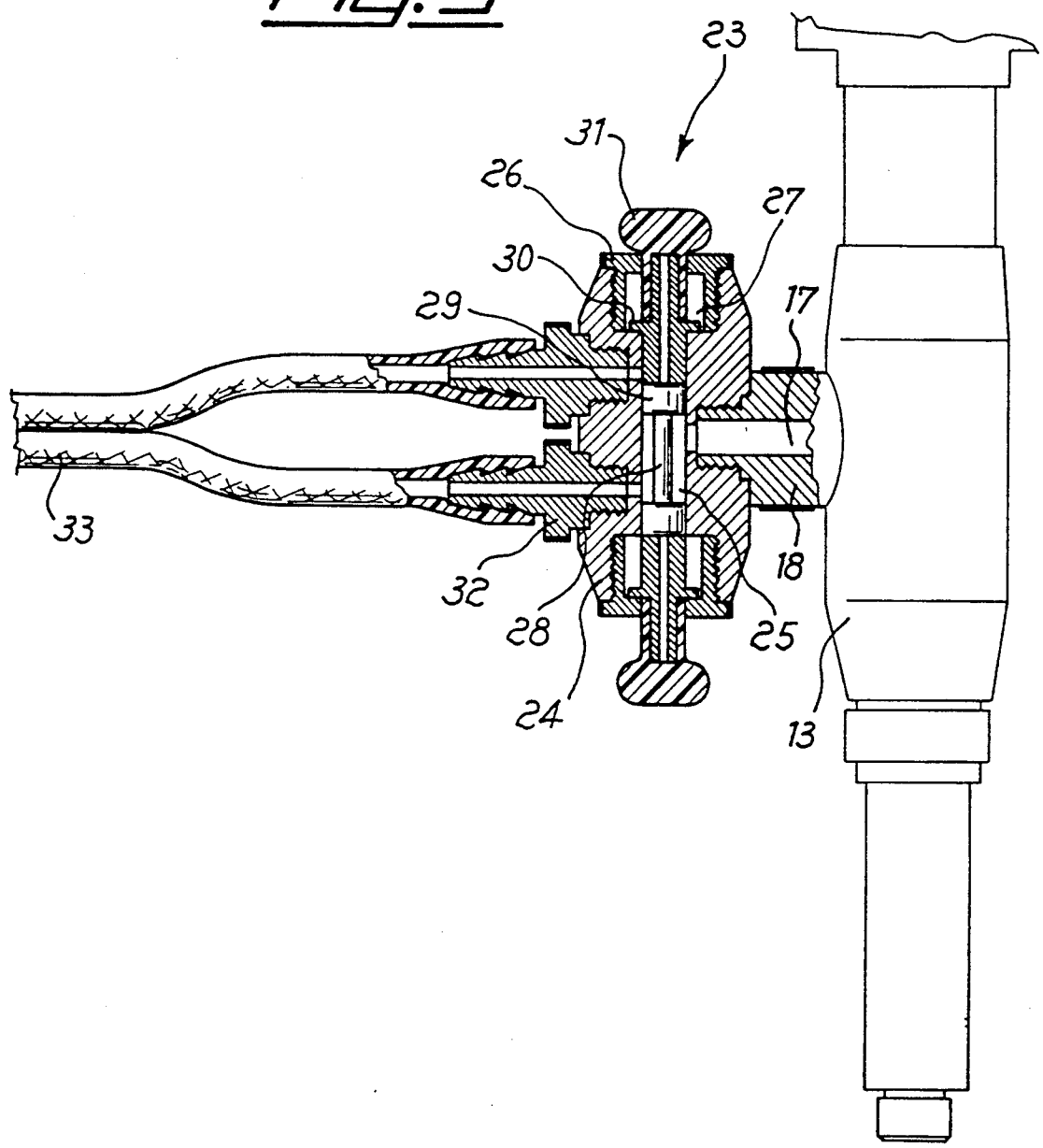

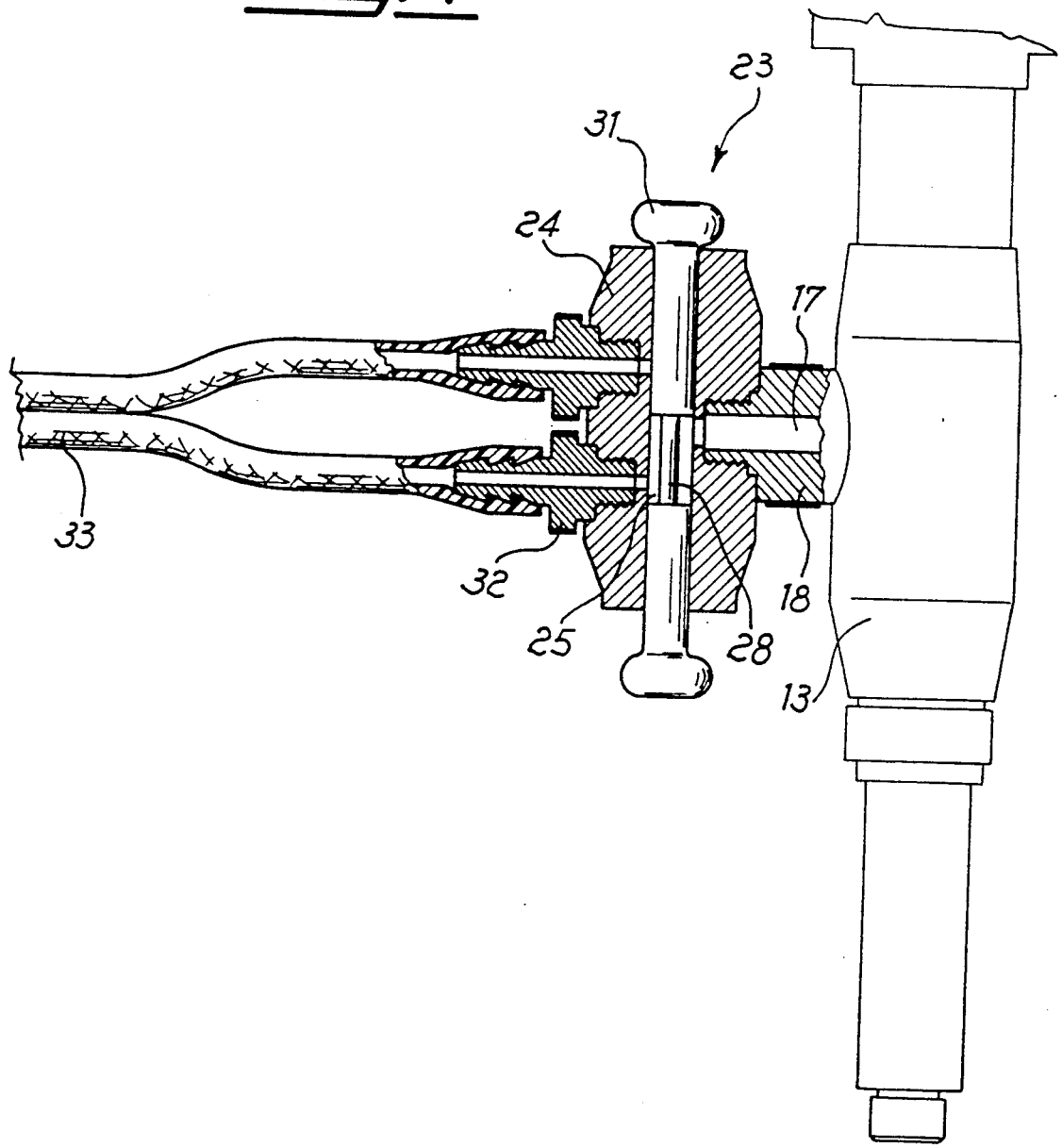

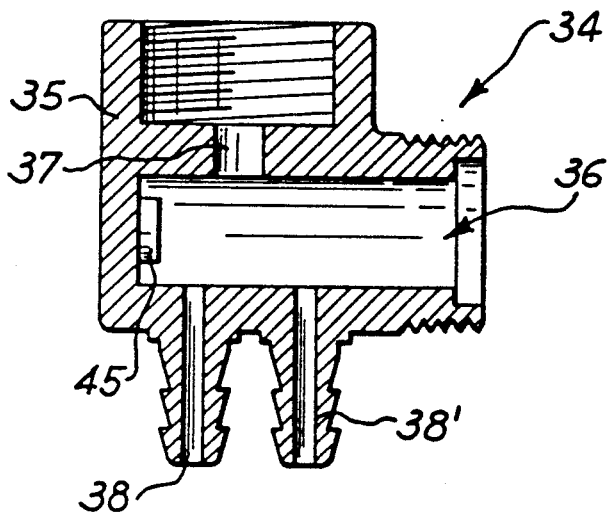
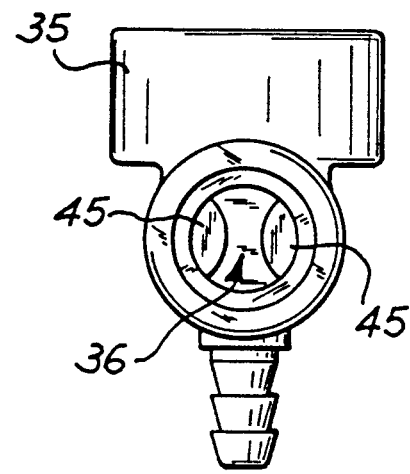
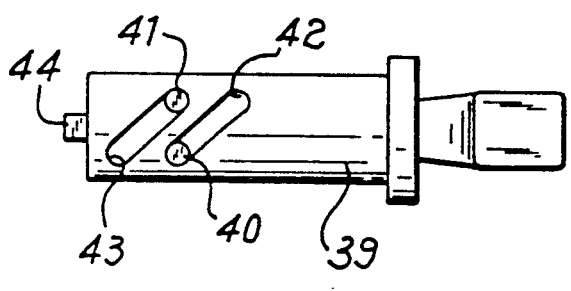
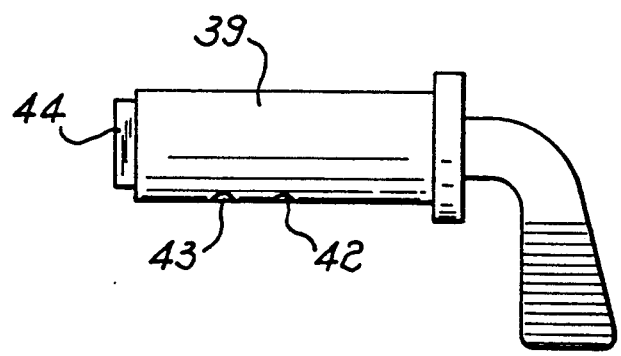
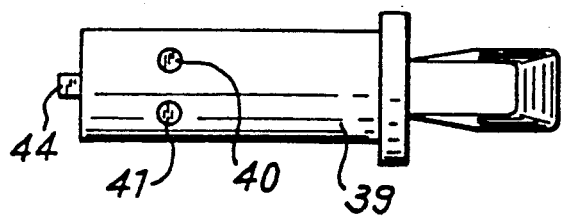

[5,171,146]

SYRINGE FOR WASHING TEETH ROOT CANALS

CROSS-REFERENCE TO RELATED APPLICATION

This application is a continuation in part of U.S. patent application Ser. No. 07/761,796, filed Sep. 16, 1991.

BACKGROUND OF THE INVENTION

The present invention refers to a syringe to be used in endodontia, namely, that branch of odontology concerned with the treatment of teeth root canals.

In the endodontic field, normal syringes for injections or considerably complicated electromechanical devices are currently used to wash the root canals of the teeth.

Considering that, for an effective washing of teeth root canals, it is usually necessary to use two liquids, in particular hydrogen peroxide and sodium hypochlorite, injected one after the other, it is immediately obvious that the instruments used up to now are quite insufficient, mainly from a practical viewpoint, in that they must be filled in sequence with said two different liquids with resulting considerable loss of time.

SUMMARY OF THE INVENTION

The aim of the present innovation is to provide a syringe for washing the root canals of the teeth comprising such a structure as to allow the automatic filling of the reservoir of the syringe itself with the first and the second of said two liquids successively, thus making the required dental operation easy and quick.

BRIEF DESCRIPTION OF THE DRAWINGS

The present invention will be better disclosed by the description of an example of a possible embodiment with reference to the accompanying drawings, where:

FIG. 2 is a longitudinal section of the syringe of FIG. 1;

FIG. 3 is a section view of the switching valve of the syringe of FIG. 1;

FIG. 4 is a sectional view of an alternative embodiment of the switching valve;

FIG. 5 is a longitudinal section of the body of a switching valve of the invention device;

FIG. 6 is a front view of FIG. 5 body; and

FIGS. 7 to 9 are respectively bottom, lateral and top views of the cock of FIGS. 5 and 6 valve.

DETAILED DESCRIPTION

Figure 1:
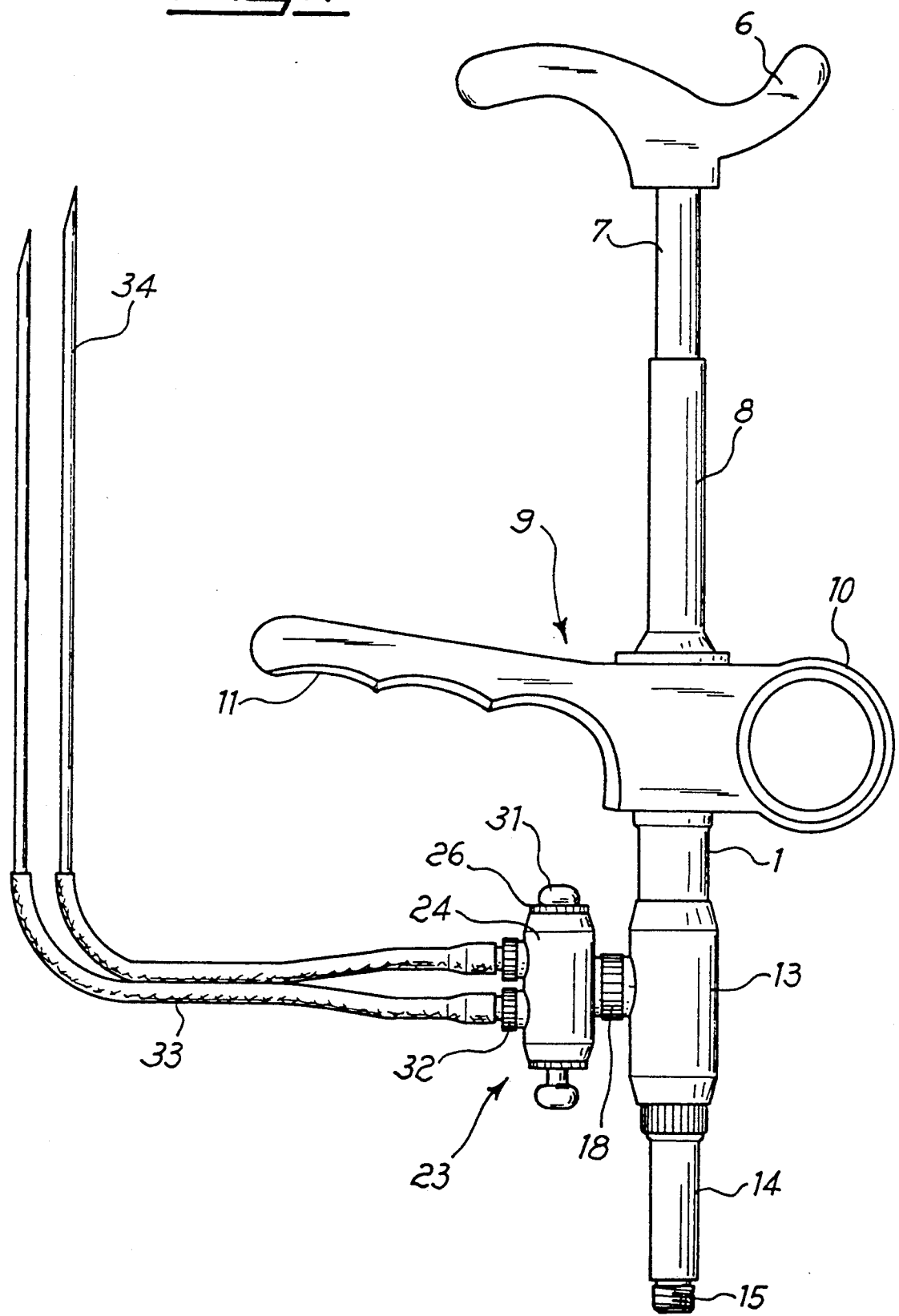
FIG. 1 is a vertical view of the syringe in question.

With reference to the above-mentioned figures, 1 refers to the syringe reservoir for the liquid to be injected consisting of a cylindrical tubular body, and 2 refers to a piston provided with a guide ring 3 made of self-lubricating material having low friction coefficient, for instance teflon, tightly slidable inside the reservoir 1 thanks to a ring seal 4.

The upper part of piston 2 is articulated to the end of a stem 5 having the other end integral to a saddle-shaped operating handgrip.

The upper portion of the stem 5 is concentrically housed in a cylindrical tubular guide 8, the lower end of which is fixed, for example by screw coupling to the top of the reservoir 1.

The central body of a handle, generally referred to with 9, is integral to the external surface of the supper portion of the reservoir 1, said central body comprising, on one side, a ring 10 for housing a thumb and, on the opposite side, an elongated element 11 with its lower side shaped in such a way as to accommodate the other fingers of the hand.

Inside sheath 7 and guide 8, a helicoidal spring 12 is housed surrounding the stem 5, one end of said spring is abutted against the bottom of the guide 8 while the opposite end is abutted against the base portion of the operating handgrip 6, said spring 12 being in the rest position when the stem 5 and relevant piston 2 are in the completely uplifted position.

To the lower end portion of reservoir 1 there is fixed, for example by screw coupling, the upper end of a two-way valve body 13, to the lower end of which is fixed, e.g., by screw coupling, an extension element 14, substantially cylindrical, axially bored, on the free end of which there is provided a connection 15, for example of the so-called American type, for fixing the needle (not shown).

The valve body 13 has a first longitudinal duct 16 coaxial to and in communication with the reservoir 1 and with said axial hole in the extension element 14, and a second transversal duct 17, perpendicular to the first one and in communication therewith, axially machined in a side duct fitting 18 fixed to the valve body 13, for instance by screw coupling.

Valve seats are respectively provided at the end of the first duct 16 connected with said axial hole in the extension element 14 and at the end of the second duct 17 connected with the first duct 16. These valve seats are equipped with seals, against which the relevant ball obturators 19 and 20 are constantly urged by helicoidal springs 21 and 22, respectively, so as to intercept any flow through said ducts, when the invention device is in its non-operative state.

Secured to the side of the fitting 18 opposite to that associated to the valve body 13, for instance by screw coupling, there is a switching valve, generally referred to with 23.

The switching valve 23, as better shown in FIG. 3, comprises a valve body 24 wherein an axial duct 25 is formed, connected with the transversal duct 17 in the two-way valve body 23, on each end of which there is provided an internally threaded cylindrical housing where a relevant headed nut is screwed, presenting a central hole coaxial and in communication with an enlarged cylindrical cavity 27 which, on its turn, is coaxial to and connected with the axial duct 25 in the valve body 24.

In said axial duct 25 and in the cavities 27 of the nuts 26 there is a slide obturator 28 consisting of an intermediate rod-shaped portion the ends of which are in a single piece with relevant enlarged cylindrical terminal portions having substantially the same diameter as that of the axial duct 25, the tight sliding movement of said terminal portions in the hole 25 being secured by relevant ring seals 29.

Each of said enlarged terminal portions of the box obturator 28 is secured to an end flange 30 and to the stem of a push-button 31 capable of sliding in a guided way in said central hole within the relevant nut 26.

In relevant cavities provided on the side of the valve body 24 opposite to that connected to the fitting 28 there are secured, for instance by screw coupling, two fittings for tubes, provided with relevant axial holes in communication with the axial duct 25 in the body 24 of the switching valve 23 each of which is connected to an end of a relevant flexible tube 33, the other end of said tube being connected to a relevant drawing tube 34 (see FIG. 1) coming from an appropriate container (not shown) for one of the relevant two liquids to be used in the dental operation.

In FIG. 4 is disclosed an alternative and simpler embodiment of the switching valve, where slide obturator enlarged terminal portions and push buttons are integral. During operation, after grasping by one hand the syringe according to the present invention by the handgrip 9, a pushing action is developed on the handle 6 in such a way as to allow the piston 2 to slide downwards in the reservoir 1 thanks to similar sliding movement of the stem 5 and relevant sheath 7 of the guide 8, with subsequent compression of the spring 12. When releasing the handle 6, the spring 12 stress relieving will bring the stem 5 and relevant piston 2 upwards thus creating a sucking force within the reservoir 1 causing the removal of the ball 20 from its seat, against the action of the spring 22, thus allowing a communication between the axial duct 25 in the body 24 of the switching valve 23 and the longitudinal duct 16 through the transversal duct 17 in the two-way valve 13 body.

In order to select the liquid to be used, the slide obturator 28 of the switching valve 23 is previously allowed to slide in the axial duct 25 as far as to bring one of the enlarged terminal portions of the intercepting position of the axial bore of the corresponding fitting for tubes 32, position determined by the counterboring of the relevant flange 30 on the annular shoulder created between the bottom of the cavity 27 and the corresponding end of the axial duct 25, connected through the relevant flexible tube 33 and the tube 34 to the container containing the liquid which has not to be drawn, said displacement of the box obturator 28 determining as a consequence the removal of the other enlarged terminal portion from the axial hole closing position of the corresponding fitting for tubes 32 so as to allow it to be connected, through the portion of the axial duct 25 of the switching valve 23 where there is said intermediate rod-shaped portion of the box obturator 28, the transversal duct 17 in the fitting 18 and the longitudinal duct 16 — which, as previously mentioned, are connected due to the removal of the ball obturator 22 from its closing position - with the inside of the reservoir 1 where, thanks to said sucking force generated in it, the first liquid will be drawn from the relevant container through the relevant tube 34 and the flexible tube 33.

A subsequent downward movement of the piston 2, according to the above-described procedure, will create inside the reservoir 1 a compression of said liquid which determines the shut down of the ball valve 20, and therefore of the transversal duct 17 and simultaneously the opening of the communication between the longitudinal duct 16 and the axial bore in the extension element 14 following to the removal of the ball obturator 19 from its seat, against the action of the spring 21, so as to allow the ejection of said first liquid through the needle (not shown) secured to the connection 15 on the free end of the extension element 14.

Once the reservoir 1 is emptied from said first liquid, the slide obturator 23 is moved, acting on the other push-button 31, to the intercepting position of the axial bore of the fitting 32 connected through the relevant flexible tube 33 and tube 34 with the container of said first liquid, thus connecting the reservoir 1 according to the same above described procedure, with the container of the second liquid in order to allow the filling of the reservoir 1 with said second liquid upon releasing of the handle 6, which will allow the spring 12 to bring the stem 5 and relevant piston 2 again to the upper starting position with subsequent generation of a resulting sucking force in the reservoir 1.

The subsequent sliding downward movement of the piston 2 by pushing, as already said, the handle 6 will allow the ejection of the second liquid through the needle as previously described.

FIGS. 5 to 9 disclose an alternative switching valve embodiment consisting in a three-way, two-positions cock. In this embodiment, the body 35 of switching valve 34 is provided with a longitudinal duct 36 having a first connection or port 37 to duct 17 of two-way valve 13, 18, and having on the opposite side two axial bores or ports 38, 38' of two fittings for feeding tubes 33 (FIGS. 5 and 6).

In longitudinal duct 36 is tightly rotatable obturator means 39 (FIGS. 7-9), consisting of the cylindrical inner part of the cock. Obturator 39 is provided with two through ducts, perpendicular and aligned to each other, 40 and 41.

While in the upper side of obturator 39 ducts 40 and 41 end with corresponding holes, in its lower side said through ducts end in correspondence with two grooves (42 and 43, respectively). Obturator 39 is also provided with a projecting portion 44 that cooperates with corresponding projecting portions 45 of longitudinal duct 36 bottom end to provide two positions for the switching valve. In a first position duct 41 is aligned with connection 37 and communications with bore 38 through groove 43. When obturator 39 is rotated in the second position, duct 40 is aligned with connection 37 and communicates with bore 38' through groove 42.

In this embodiment, switching valve 34 is obtained by injection molding of thermoplastic resins and, most preferably, also elements 6, 10-11, 13, 18 and 14 are made in the same way.

The present invention is not limited to the described embodiment, but it comprises any other possible variants in the configuration.

What is claimed is:

1. A syringe for washing teeth root canals comprising:

a reservoir for containing a liquid to be injected, the reservoir having an upper and a lower end;

a piston capable of tightly sliding inside said reservoir;

a stem having an end connected to said piston while the opposite upper end is fixed to operating means;

a tubular sheath having an upper and lower end, the upper end thereof being secured to said operating handle, in which the upper portion of said stem is concentrically housed;

guide means having a lower end of which is secured to the upper end of said reservoir to slidingly guide said stem and said tubular sheath.

spring means for urging upwardly said stem to return said piston from the lower position to the uplifted position inside said reservoir; two-way valve means having an upper and lower end provided at the bottom of said reservoir, in the body of which there is provided a longitudinal duct having upper and lower end, the upper end of which is in communication with said reservoir and the lower end of which is provided with a first obturator constantly urged in the closing position by means of first spring means, and a transversal duct, having an end coming out in said longitudinal duct provided with a second obturator constantly urged in the closing position by means of second spring means;

an extension element, extending from the lower end of said two-way valve means, wherein an axial bore is provided in communication with said longitudinal duct in said two-way valve means downstream of said first obturator and presenting on the free end a connection for fixing a syringe needle;

a switching valve connected to said two-way valve and having a body in which a longitudinal duct is provided, connected at a first side with said transversal duct of said two-way valve means and at the opposite side with relevant axial bores of two fittings for tubes secured to said body, in which longitudinal duct there is tightly movable obturator means capable of being manually displaced so as to alternatively connect said longitudinal duct and one, or the other, of said axial bores of said fittings for tubes; two flexible tubes having first ends connected to relevant ones among said fittings for tubes, and second ends opposite to the first ones connected to respective drawing tubes of relevant different liquids contained in a suitable container; and a handgrip for grasping said syringe by one hand.

2. A syringe according to claim 1, wherein the lower end of said stem is articulated to said piston.

3. A syringe according to claim 1, wherein said first and second obturator in said longitudinal duct and said transversal duct respectively, in said two-way valve body, consist of a ball obturators.

4. A syringe according to claim 1, wherein said first and second spring means is capable of constantly urging said first and second obturator in the closing position of said longitudinal duct and said transversal duct respectively, in said two-way valve body consist of helicoidal springs.

5. A syringe according to claim 1, wherein said obturator in said longitudinal duct of said switching valve consist of a slide obturator having its enlarged terminal portions connected to an intermediate rod-shaped portion and provided with push-buttons.

6. A syringe according to claim 1, wherein said handgrip comprises a central body, integral to an upper perimetral portion of said reservoir, provided on one side with an annular element and on the opposite side with an elongated grip element.

7. A syringe according to claim 1, wherein said obturator in said longitudinal duct of said switching valve is a three-way two-position shocking cock.

* * * * *